United States Patent [19]

Montagnier et al.

[11] Patent Number: 5,610,035

[45] Date of Patent: Mar. 11, 1997

[54] METHODS FOR THE PREPARATION OF HYBRIDOMAS PRODUCING LYMPHADENOPATHY-ASSOCIATED VIRUS (LAV) GP110-SPECIFIC MONOCLONAL ANTIBODIES AND METHODS FOR THE PURIFICATION OF GP110 EMPLOYING SAID MONOCLONAL ANTIBODIES

[75] Inventors: Luc Montagnier, Le Plessis Robinson; Bernard Krust, Paris; Solange Chamaret, Paris; Francois Clavel, Paris; Jean-Claude Chermann, Elancourt; Francoise Barre-Sinoussi, Issy les Moulineaux, all of France

[73] Assignee: Institut Pasteur Centre National de la Recherche Scientific, Paris, France

[21] Appl. No.: 313,572

[22] Filed: Sep. 27, 1994

Related U.S. Application Data

[60] Continuation of Ser. No. 950,294, Sep. 24, 1992, Pat. No. 5,407,811, which is a division of Ser. No. 647,209, Jan. 28, 1991, abandoned, which is a continuation of Ser. No. 494,858, Mar. 14, 1990, which is a continuation of Ser. No. 279,280, Dec. 2, 1988, abandoned, which is a continuation of Ser. No. 771,247, Sep. 30, 1985, abandoned, which is a continuation-in-part of Ser. No. 771,230, Aug. 30, 1985, which is a continuation-in-part of Ser. No. 706,562, Feb. 28, 1985, abandoned, which is a continuation-in-part of Ser. No. 558,109, Dec. 5, 1983, abandoned.

[30] Foreign Application Priority Data

Oct. 18, 1984 [FR] France .................... 84 16013

[51] Int. Cl.$^6$ .......... C12P 21/04; C12P 21/08; C07K 16/00; A23J 1/00
[52] U.S. Cl. .................. 435/70.21; 530/388.35; 530/412; 530/413; 424/208.1
[58] Field of Search .......... 435/7.1, 70.1, 435/172.2, 240.27; 530/388.1, 388.35; 424/148.1; 935/89

[56] References Cited

U.S. PATENT DOCUMENTS

| | | |
|---|---|---|
| 4,520,113 | 5/1985 | Gallo et al. . |
| 4,629,783 | 12/1986 | Cosand . |
| 4,716,102 | 12/1987 | Levy .......................................... 435/5 |
| 4,725,669 | 2/1988 | Essex et al. . |

FOREIGN PATENT DOCUMENTS

| | | |
|---|---|---|
| 0113078 | 7/1984 | European Pat. Off. . |
| 0115459 | 8/1984 | European Pat. Off. . |
| WO84/04327 | 11/1984 | WIPO . |
| WO86/02383 | 4/1986 | WIPO . |
| WO87/02988 | 5/1987 | WIPO . |

OTHER PUBLICATIONS

Goodenow et al., 1989, "HIV-1 isolates are rapidly evolving quasispecies: evidence for viral mixtures and preferred nucleotide substitutions", J. Acquir. Immune Defic. Syndr. 2(4):344–52.

Wolfs et al., 1990, "Evolution of sequences encoding the principal neutralization epitope of human immunodeficiency virus 1 is host dependent, rapid, and continuous", Proc. Natl. Acad. Sci. USA 87(24):9938–42.

Watkins, et al., 1993, "Immune escape by human immunodeficiency virus type 1 from neutralizing antibodies: evidence for multiple pathways", J. Virol. 67(12):7493–7500.

Geysen et al., 1988, "Cognitive features of continuous antigenic determinants", J. Molec. Recog. 1:33–41.

Sarngadharan et al., 1985, "Immunological properties of HTLV–III antigens recognized by sera of patients with AIDS and AIDS–related complex and of asymptomatic carriers of HTLV–III infection", Cancer Res. 45:4574s–4577s.

Schneider et al., 1982, "A one-step purification of membrane proteins using a high efficiency immunomatrix", J. Biol. Chem. 257(18):10766–10769.

Kitchen et al, "Aetiology of AIDS—Antibodies to Human T–Cell Leukaemia Virus (Type III) in Haemophiliacs," Nature, 312, 367–369 (1984).

Essex et al., "Antibodies to Cell Membrane Antigens Associated with Human T–Cell Leukemia Virus in Patients with AIDS," Science, 220, 859–862 (1983).

Dreesman et al., "Antibody to Hepatitis B Surface Antigen After a Single Inoculation of Uncoupled Synthetic HBsAq Peptides," Nature, 295, 158–160 (1982).

Scheupbach et al., "Serological Analysis of a Subgroup of Human T–Lymphotropic Retroviruses (HTLV–III) Associated with AIDS," Science, 224, 503–505 (1984).

Kalyanaraman et al., "Antibodies to the Core Protein of Lymphadenopathy–Associated Virus (LAV) in Patients with AIDS," Science, 225, 321–323 (1984).

Robey et al., "Characterization of Envelope and Core Structural Gene Products of HTLV–III with Sera from AIDS Patients," Science, 228, 593–595 (1985).

Allan et al., "Major Glycoprotein Antigens That Induce Antibodies In AIDS Patients Are Encoded by HTLV–III," Science, 228, 1091–1094 (1985).

(List continued on next page.)

Primary Examiner—Christine M. Nucker
Assistant Examiner—Jeffrey S. Parkin
Attorney, Agent, or Firm—Finnegan, Henderson, Farabow, Garrett & Dunner, L.L.P.

[57] ABSTRACT

A novel human retrovirus which is the aetiological agent of acquired immune deficiency syndrome (AIDS), designated lymphadenopathy-associated virus (LAV), was isolated from the lymph nodes of a patient suffering from generalized persistant lymphadenopathy. LAV displays a tropism for $CD4^+$ lymphocytes, a $Mg^{2+}$-dependent reverse transcriptase (RT) activity, a density of 1.16–1.17 as determined by sucrose gradient centrifugation, a particle diameter of 139 nm, and a p25 antigen that is immunologically distinct from the HTLV-I/II p24 protein. Radioimmunoprecipitation analysis (RIPA) of $^{35}$S-cysteine-labeled viral or cellular lysates employing patient antisera resulted in the identification of a viral antigen having a molecular weight of 110 kDa. Endoglycosidase treatment of this antigen produces a protein with a molecular weight of 90 kDa. Methods are disclosed for the preparation of hybridomas producing LAV gp110-specific monoclonal antibodies (Mabs). Methods are also disclosed employing these MAbs in the purification of the LAV envelope glycoprotein, gp110.

3 Claims, 2 Drawing Sheets

OTHER PUBLICATIONS

Crowl et al., *Chemical Abstracts*, 103, p. 190, No. 154983e (1985).

Montagnier et al., *Chemical Abstracts*, 103, p. 263, No. 34641v (1985).

Weiss et al., "Neutralization of Human T–Lymphotropic Virus Type III by Sera of AIDS and AIDS–Risk Patients," *Nature*, 316, 69–72 (1985).

Barin et al., "Virus Envelope Protein of HTLV–III Represents Major Target Antigen for Antibodies in AIDS Patients," *Science*, 228, 1094–1096 (1985).

Wain–Hobson et al., "Nucleotide Sequence of the AIDS Virus, LAV," *Cell*, 40, 9–17 (1985).

Muesing et al., "Nucleic Acid Structure and Expression of the Human AIDS/Lymphadenopathy Retrovirus," *Nature*, 313, 450–458 (1985).

Schneider et al., *Chemical Abstracts*, 103, p. 430, No. 52370k (1985).

Sarnqadharan et al., *Chemical Abstracts*, 103, p. 551, No. 121329t (1985).

Alizon et al., "Molecular Cloning of Lymphadenopathy–Associated Virus," *Nature*, 312, 757–760 (1984).

Chang et al., "An HTLV–III Peptide Produced by Recombinant DNA is Immunoreactive with Sera from Patients with AIDS," *Nature*, 315, 151–154 (1985).

Chang et al., "Detection of Antibodies to Human T–Cell Lymphotropic Virus–III (HTLV–III) with an Immunoassay Employing a Recombinant *Escherichia coli* Derived Viral Antigenic Peptide," *Biotechnology*, 3, 905–909 (1985).

Schneider et al. "A Glycopolypeptide (gp 100) is the Main Antigen Detected by HTLV–III Antisera," *Med. Microbiol. Immunol.*, 174, 35–42 (1985).

Allain et al., "Serological Markers in Early Stages of Human Immunodeficiency Virus Infection in Haemophiliacs," *The Lancet*, 2(8518), pp. 1233–1236 (1986).

Rasheed et al., "Virus–Neutralizing Activity, Serologic Heterogeneity, and Retrovirus Isolation From Homosexual Men in the Los Angeles Area," *Virology*, 150, pp. 1–9 (1986).

Montagnier et al., "Identification and Antigenicity of the Major Envelope Glycoprotein of Lymphadenopathy–Associated Virus," *Virology*, 144, pp. 283–289 (1985).

Gallo et al., "The Chronology of AIDS Research," *Nature*, 326, pp. 435–436 (1987).

Montagnier et al., "The AIDS Virus: Structure and Variation," in AIDS: The Safety of Blood and Blood Products, Petricciani et al., eds., pp. 1–10 (World Health Organization, John Wiley& Sons, 1987).

Clavel et al., "Deficient $LAV_1$ Neutralising Capacity of Sera From Patients With AIDS or Related Syndromes," *The Lancet*, pp. 879–880 (Apr., 1985).

Brucker et al., "HIV–2 Infection in Two Homosexual Men in France," *The Lancet*, p. 223 (Jan., 1987).

Coffin et al., "Human Immunodeficiency Viruses," *Science*, 232, p. 697 (1986).

*Biotechnol. Newswatch*, vol. 5, p. 3, Abstract No. 03-10-003226 (1985).

METHODS FOR THE PREPARATION OF HYBRIDOMAS PRODUCING LYMPHADENOPATHY-ASSOCIATED VIRUS (LAV) GP110-SPECIFIC MONOCLONAL ANTIBODIES AND METHODS FOR THE PURIFICATION OF GP110 EMPLOYING SAID MONOCLONAL ANTIBODIES

CROSS-REFERENCE TO RELATED APPLICATIONS

This application is a continuation of application Ser. No. 07/950,294, filed Sep. 24, 1992, now U.S. Pat. No. 5,407,811, which is a division of application Ser. No. 07/647,209, filed Jan. 28, 1991, now abandoned, which is a continuation of application Ser. No. 07/494,858, filed Mar. 14, 1990, which is a continuation of application Ser. No. 07/279,280, filed Dec. 2, 1988, now abandoned, which is a continuation of application Ser. No. 06/771,247, filed Sep. 30, 1985, now abandoned, which is a continuation-in-part of 06/771,230, filed Aug. 30, 1985, which is a continuation-in-part of application Ser. No. 06/706,562, filed Feb. 28, 1985, now abandoned, which is a continuation-in-part of application Ser. No. 06/558,109, filed Dec. 5, 1983, now abandoned.

The present invention relates to a purified virus of Lymphadenopathy (denoted below by the abbreviation LAS) and of Acquired Immunodeficiency Syndrome (denoted below by the abbreviation AIDS), to a process for producing antigens of the envelopes of these viruses, and their use in the preparation of immunogenic compositions for the diagnosis of LAS and AIDS.

BACKGROUND OF THE INVENTION

A retrovirus showing characterizations of the etiological agent of AIDS has been identified. It was first described in an article of Barre-Sinoussi et al., Science, 220, 868 (1983).

This retrovirus has the following characteristics. It is T-lymphotropic; its preferred target is constituted by Leu 3 cells (or T4 lymphocytes); it has reverse transcriptase activity requiring the presence of $Mg^{2+}$ and exhibits strong affinity for poly(adenylate-oligodeoxy-thynidylate) [poly(A)-oligo(dT) 12–18]; it has a density of 1.16–1.17 in a sucrose gradient, an average diameter of 139 nanometers; and a nucleus having an average diameter of 41 nanometers; the lysates of this virus are recognized immunologically, these lysates contain a protein p25 recognized by the same sera but which is not recognized immunologically by the p24 protein of the HTLVI and II viruses.

Retroviruses of this type (sometimes denoted by the genetic abbreviation LAV) have been deposited in the National Collection of Micro-organism Cultures of the INSTITUT PASTEUR of Paris 28 rue du Docteur Roux, 75724 Paris Cedex 15, under numbers I-232, I-240 and I-241. Morphologically and immunologically similar virus strains have been isolated in other laboratories; the retrovirus strain HTLV-III (Gallo et al., Science, 224, 500 (1984); Sarngadharan et al., Science 224, 506 (1984); and ARV isolated by Levy et al., Science, 225, 840–842 (1984). Reference is also made to European patent application filed Sep. 14, 1984, with the priority of British patent application No. 83 24800, filed Sep. 15, 1983, which corresponds to U.S. Ser. No. 06/558,109, filed Dec. 5, 1983, now abandoned, as regards a more detailed description of the LAV retroviruses and uses of extracts of these viruses.

Only the core antigens of the virus could be recognized, alter lysis of the virus, by sera of patients infected with AIDS or LAS. A protein p41 has been described in the above articles on HTLV3 as a possible component of the envelope of the virus. However, formal proof that p41 was a protein of the envelope has not been forthcoming.

Processes for obtaining a LAV virus or a related virus have also been described. Barre-Sinoussi et al., cited above describes the preparation of the virus in T lymphocyte cultures derived either from blood, or from the umbilical cord, or from bone marrow cells of adult donors in good health. This process comprises particularly the following essential steps:

- viral infection of the T lymphocytes, after activation by a mitogenic lectin, with a viral suspension derived from a crude supernatant liquor of lymphocytes producing the virus (initially obtained from a patient infected with AIDS or LAS),
- culturing of cells infected with TCGF, in the presence of anti-α-interferon sheep serum,
- purification of the virus produced (production commences generally the 9th and the 15th day following the infection and lasts 10 to 15 days) by precipitation of the virus in polyethyleneglycol to produce a concentrated sample of the virus, then centrifuging the preparation in a sucrose gradient of 20 to 60% or in isotonic gradient of metrozanide (sold under the trade mark NYE-GAARD™ by NYEGAARD™, Oslo). The virus is then recovered with a strip of suitable density 1.16–1.17 in the case of the sucrose gradient or 1.10–1.11 in a NYCODENZ™ gradient.

The LAV virus may also be produced from continuous cell lines of type T, such as the CEM cell line, or from B lymphoblastoid cell lines, such as obtained by the transformation of the lymphocytes derived from a healthy donor with the Epstein-Barr virus. The cell lines obtained continuously produce a virus (LAV-B) which possesses the essential antigenic and morphological lines of the LAV viruses (except that it is collected in a strip of density sometimes slightly higher than in the preceding case, particularly 1.18) in sucrose. The final purification of the virus can also be carried out in a NYCODENZ™ gradient. Reference can also be made to general techniques of producing virus type B-LAV, French patent application, 84 07151, filed May 9, 1984.

DETAILED DESCRIPTION OF PREFERRED EMBODIMENTS

Figure 1:
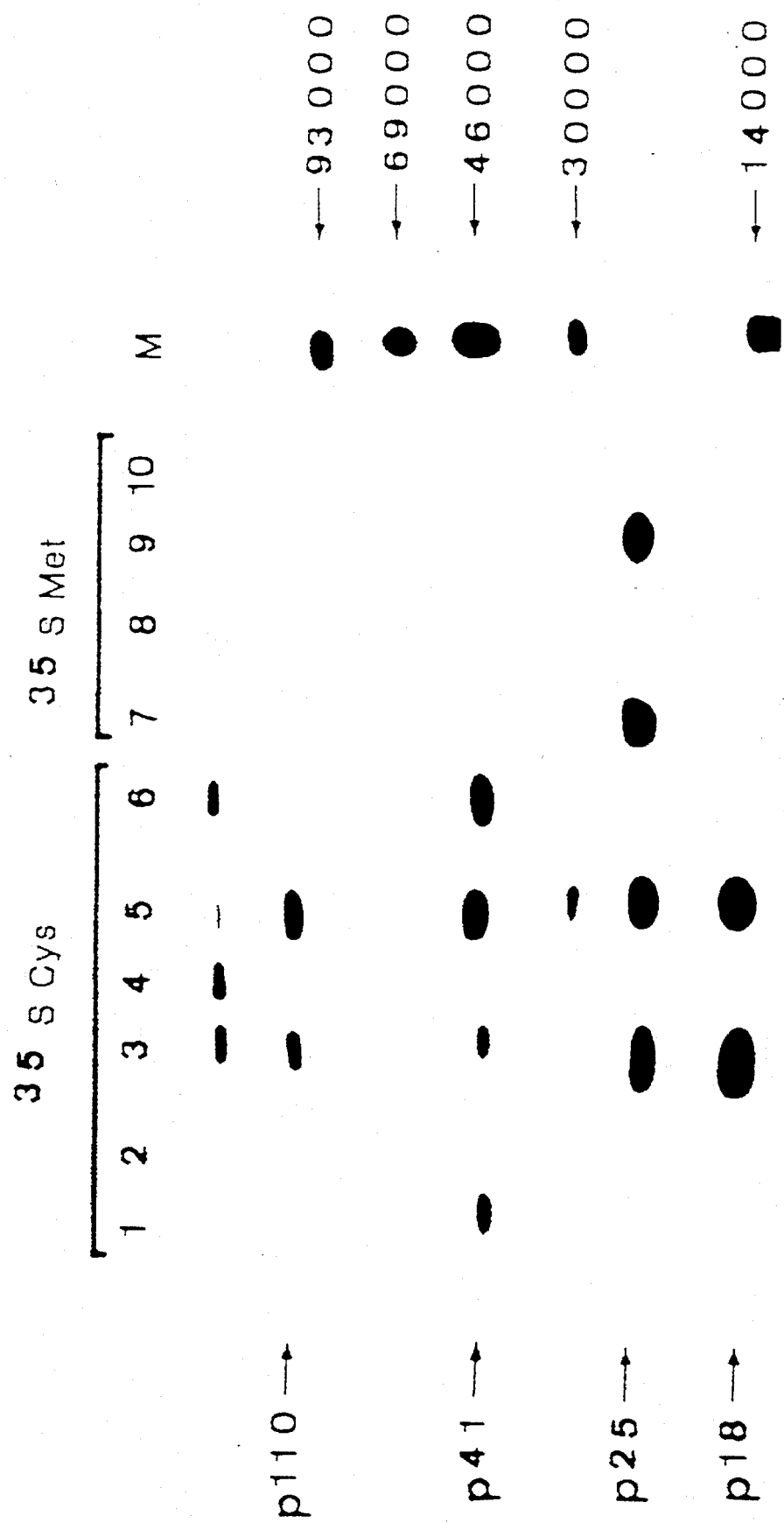
FIG. 1 is a photographic reproduction of gel strips used in the electrophoresis of lysate extracts of T lymphocytes infected with LAV, and uninfected T lymphocytes (controls).

The invention relates to a novel variety of purified retroviruses, related to the retrovirus defined above, but which are distinguished therefrom (or which is characterized) in that these viruses include one or several antigens having the characteristics of a glycoprotein in the tests which are described below. These antigens can be detected by labeling the virus with labeled cysteine, particularly $^{35}$S-cysteine, in sufficiently high concentration in the culture medium of the virus, particularly 200 microcuries per ml of medium;

wherein the culture medium is devoid of unmarked cysteine. These antigens are selectively recognized by sera of patients afflicted with AIDS or LAS or by the sera of asymptomatic carriers of the virus.

A preferred antigen, according to the preceding definition, obtained from a lysate of this virus (or by gentle scouring of the envelopes of the virus), has a molecular weight of about 110,000 daltons. This molecular weight can be compared with known molecular weight (MW) standards in a comparison of migration distances employing gel electrophoresis. In particular, the following proteins (marketed by AMERSHAM™) are employed:

lysozyme-($^{14}$C)-methyl(MW: 14,300), carbon dioxide-($^{14}$C)-methyl (MW: 30,000), ovalbumin-($^{14}$C)-methyl (MW: 46,000), bovine albumin serum (14C)-methyl (MW: 69,000), phosphorylase b-($^{14}$C)-methyl (MW: 92,500), myosin-($^{14}$C)-methyl (MW: 200,000).

The gel electrophoresis was carried out on a 12.5% gel, then under a voltage of 35 V for 18 hours.

The invention also relates to antigens of the retrovirus, particularly antigens having a molecular weight of about 100,000. The antigens are recognized by sera of patients infected with AIDS or LAS or by sera of persons who have been exposed to LAV viruses, or viruses analogous with the latter. These antigens also form complexes with concanavalin A, said complex being dissociatable in the presence of O-methyl-α-D-mannopyranoside. The antigens according to the invention can also form complexes with other lectins. For example, those known as LENTYL-LECTIN. The preferred antigen according to the invention, having a molecular weight of about 100,000, is also sensitive to the action of endoglycosidases. On exposure to an endoglycosidase, the antigen having a molecular weight of about 100,000 produces a protein having a molecular weight of about 90,000, the latter being separable by, for example, immunoprecipitation or gel electrophoresis.

The preferred antigens of the invention are constituted by glycoproteins.

The invention also relates to the process for producing the viruses according to the invention. This process is distinguished from the processes described above in the method of final purification. In particular, the purification step of the process according to the invention does not employ gradients but involves performing differential centrifugations on the supernatants of the culture media of the producing cells. This process comprises a first centrifugation at an angular centrifugation velocity, particularly of about 10,000 rpm, enabling the removal of non-viral constituents, more particularly of cellular constituents, followed by a second centrifugation at a higher angular velocity, particularly at about 45,000 rpm, to precipitate the virus itself. In preferred embodiments, the first centrifugation, at 10,000 rpm, is maintained for 10 minutes and the second at 45,000 rpm, for 20 minutes. These are only indicative values, and it is within the ability of the specialist to modify the centrifugation conditions to ensure the separation of the cellular constituents and the viral constituents.

This modification of the purification process results in the production of viral preparations from which the characterized antigen can be isolated. This antigen has not been obtained from virus preparations purified by the previous methods. The viruses obtained by the process of the present invention are distinguished from the preceding viral preparations, in that they are recognized by sera of patients or of persons who have been exposed to the LAV virus or to morphologically and antigenically similar strains.

The antigen according to the invention can be obtained from these viruses by lysis (or other suitable processing) of the viruses in the presence of any suitable detergent and by recovery and separation of the liberated antigens. Advantageously, the lysis of the virus is effected in the presence of aprotinin or any other agent suitable for inhibiting the action of proteases. The separation of the antigens according to the invention can then be carried out by any method known: for example, it is possible to separate the proteins by employing their different migration distances in a predetermined gel, the desired protein is then isolated from the band of the gel in which it would normally be found in an electrophoresis process under determined conditions, having regard to its molecular weight. The antigen according to the invention can be separated from the lysate of the above viruses, due to their affinity for lectins, in particular, concanavalin A or lentyl-lectine. The lectin used is preferably immobilized on a solid support, such as the agarose-based cross-linked polymer marketed under the trade mark SEPHAROSE®. After contacting the lysate with a suitable buffer, the antigen retained can be eluted in any suitable manner, particularly by employing O-methyl-α-mannopyranoside in solution.

A more thorough purification of these antigens can be performed by immuno-precipitation with sera of patients known to possess antibodies against this protein, with concentrated antibody preparations (polyclonal antibodies) or with monoclonal antibodies, more particularly directed against the antigen of the invention, in particular, the antigen having a molecular weight of about 110,000, denoted below by the abbreviation gp110.

Additional characteristics of the invention appear in the following description of the isolation of a virus according to the invention, and of an envelope antigen of the virus. Reference is also made to FIG. 1, which is a photographic reproduction of gel strips which been used to carry out electrophoresis of lysate extracts of T lymphocytes, respectively infected and uninfected (controls) by a LAV suspension.

T lymphocytes derived from a healthy donor and infected with LAV1, under the conditions described by Barre-Sinoussi et al., or CEM cells derived from a patient afflicted with leukemia and infected in vitro with LAV1, were cultured in a medium containing 200 microcuries of $^{35}$S-cysteine and devoid of marked cysteine. The infected lymphocytes were cultured in a non-denaturing medium to prevent the degradation of the antigen sought. The supernatant liquor from the culture medium is then centrifuged at 10,000 rpm for 10 minutes to remove the non-viral constituents, followed by a second centrifugation at 45,000 rpm for 20 minutes, to produce the sedimentation of the virus. The virus is then lysed with a detergent in the presence of aprotenin (5%), particularly under the conditions described by Barre-Sinoussi et al.

The same process is repeated on lymphocytes coming from a healthy donor as a control.

The various lysates were then immuno-precipitated by sera of patients infected with AIDS or with SLA, as well as from healthy donors or donors only infected with other diseases. The media were then electrophoresed in a SDS-polyacrylamide gel.

The results are shown in FIG. 1. The gel strips numbered from 1 to 6 were obtained from preparations labeled with $^{35}$S-cysteine. The strips numbered 7 to 10 correspond to the results observed on infected or uninfected lymphocyte preparations labeled with $^{35}$S-methionine. Finally, the strip M corresponds to the migration distances of the reference proteins identified above. The molecular weights of the reference proteins are recited in the right hand portion of the figure. To the left of the figure are referenced the labeled viral proteins.

It is noted that columns 7 to 10 show protein p25 of LAV, marked with $^{35}$S-methionine. This protein is absent from the columns 8 to 10 corresponding to results obtained from healthy lymphocytes.

The columns 3 and 5 correspond to the results observed on preparations obtained from lymphocytes infected and marked with $^{35}$S-cysteine. The proteins p25 and p18 were characteristic of proteins of the nucleotide of LAV and the glycoprotein gp110, also specific of LAV. There also appear in the various preparations, although less distinctly, images corresponding to a protein p41 (molecular weight of the order of 41,000), non-specific to the LAV virus. This protein is also observed in the controls.

The virus according to the invention and the antigen according to the invention can be either precipitated by lectins, particularly concanavalin A, or fixed to a SEPHAROSE®-concanavalin A column. This fixation comprises contacting the lysate of the above virus in a buffer to form the following composition:

| Tris | 10 mM |
|---|---|
| NaCl | 0.15 M |
| CaCl | 1 mM |
| MgCl | 1 mM |
| Detergent marketed under the trademark TRITON ™ | 1% |
| pH | 7.4 |

Once the fixation has been effected, the SEPHROSE®-concanavalin A is washed with a buffer of the same composition, except that the TRITON™ is lowered to 0.1%. The elution is then effected with an 0.2M o-methyl-α-D-mannopyranoside solution in the washing buffer.

The protein may be further concentrated by immuno-precipitation with antibodies contained in the sera of patients infected with AIDS, or with polyclonal antibodies obtained from a serum derived from an animal previously immunized against the virus of the invention, or the above glycoprotein. The protein can then be recovered by dissociation of the complex employing a solution having an adequate content of ionic salt.

Preferably the above antibody preparation have been previously immobilized on an insoluble support of the SEPHAROSE® B type.

It is also possible to employ monoclonal antibodies secreted by hybridomas previously prepared against gp110. These monoclonal antibodies, as well as the hybridomas which produce them, also form part of the invention.

Below are described the conditions under which the monoclonal antibodies according to the invention can be prepared.

Immunization of the Mice

Groups of Balb/c mice aged from 6 to 8 weeks were used. One group received the virus containing the above glycoprotein, another the glycoprotein gp110. The immunization procedure, identical for the 4 mice, consisted of an injection, intraperitoneally, with three repeats, followed by one injection intravenously of 10 mg of the antigenic preparation, in the presence of Freund complete adjuvant at day 0, Freund incomplete adjuvant at day 0, Freund incomplete adjuvant at day 14, and without adjuvant at days 28 and 42.

Fusion and Culture of the Hybrids

The variant 6.53 which does not secrete myeloma P3×63 Ag8, is resistant to azaguanine, and which is derived from the cell line MOPC-21, was used. Fusion with immunized mouse splenocytes was carded out in the presence of polyethylene-glycol 4000 by the technique of FASEKAS DE ST-GROTH and SCHEIDEGGER on the 45th day (8). The selection of the hybrids in RPMI 16–40 "HAT" medium was carded out by the same culture in 24 plates (Costar).

The hybridomas producing antibodies of adequate specificity were then cloned in plates of 96 cups, in the presence of a "feeder" layer of syngenic thymocytes. The producing clones selected were then expanded in 24 cup plates, still in the presence of thymocytes. When the confluence appeared in one of the cups, the clone was injected intraperitoneally into a BALB/c mouse which had received an injection of Pristane 8 days previously, and/or kept in liquid culture.

Demonstration of the Anti-LAV Antibodies

Five different techniques enabled the characterization of the clones which produced antibodies of interesting specificity. In a first stage, the hybrids producing antibodies were determined by an ELISA test revealing mouse immunoglobulins in the supernatant liquors. From this first selection, supernatants were selected which had antibodies directed against viral constituents as shown by an ELISA test revealing anti-LAV antibodies (9), or by immunofluorescence on the virus producing human cells. Finally, the supernatant liqours were analyzed by radioimmunoprecipitation of virus labeled with cysteine and by the technique of Western-Blot on viral preparation (10), which permitted the determination of the specificities of these anti-LAV antibodies.

RESULTS

Cells obtained from the various fusions were cultured in 648 cups. Their microscopic examination has shown that the majority of these cups contained a single hybrid clone capable of growing in a "HAT" selective medium. More than 50% of the samples produced antibodies giving rise to a positive response on ELISA antivirus examination. The most representative fusions were tested by the Western-Blot technique and several of the fusions were subcloned, taking into account their specificity, their reactivity in antivirus ELISA and their behavior in cultivation. The hybrids which produced antibodies which recognized gp110 were preferably selected. All of the subclones produced antibodies which, after expression, were injected into syngenic mice. Analysis of the specificities of the antibodies present in the different ascites liquids confirm the specificity of the antibodies of said ascites with respect to gp110.

The monoclonal antibodies obtained can be employed to purify proteins containing an antigenic site also contained in gp110. The invention relates therefore, to these processes of purification. This process is advantageously applied to virus lysates, or T lymphocytes lysates, or other cells producing LAV or the like, when before the lysis is performed care is taken to avoid the uncontrolled separation of gp110 (this process can also be applied to any solution containing gp110 or a protein, polypeptide or glycoprotein comprising an antigenic site of an envelope protein recognized by the monoclonal antibody, whatever the nature of this solution). For practicing this process, the monoclonal antibodies are advantageously immobilized on a solid support, preferably adapted to affinity chromatography operations. For example, these monoclonal antibodies are fixed on an agarose lattice with three-dimensional cross-linking, marketed under the trade mark SEPHAROSE® by the Swedish company PHARMACIA A.G., for example, by the cyanogen bromide method.

The invention therefore relates more particularly to a process for separating the antigens characterized by processes comprising contacting the culture medium which may contain the antigens with an affinity column having the above monoclonal antibodies, to selectively fix said polypeptides, proteins or glycoproteins, and then to recover the latter by dissociating the antigen-antibody complex formed by employing a suitable buffer, particularly a solution of adequate ionic strength, for example, of a salt, preferably ammonium acetate (which does not leave a residue when freeze drying of the preparation is then carried out). It is also possible to employ a solution acidified to pH 2–4 or to a glycine buffer at the same pH.

These antigens can be employed as reagent or as in vitro diagnostic agents for the detection of anti-LAV antibodies. It is self-evident that the invention relates also to polypeptide fractions which can have lower molecular weights, when the polypeptide fractions carry antigenic sites recognizable by the same monoclonal antibodies. It will be clear to the specialist that the monoclonal antibodies of the invention enable the isolation, from the above-indicated antigens, of smaller peptide sequences containing the same antigenic sites, for example, by using known techniques of cutting up the original polypeptide employing enzymes capable of cleaving the larger polypeptides at specific sites. As an example, the enzyme of *Staphilococcus aureus* V8, alpha-chymotrypsine; "mouse sub-maxilllary gland protease" marketed by the BOEHRINGER™ company, Vibrio alginolyticus chemovar iophagus collagenase, specifically recognizes the peptides Gly-Pro and Gly-Ala, etc.

It is also possible to isolate polypeptides or fragments of antigens of envelopes of the virus, by cloning fragments excised from a cDNA constructed from genomes of the various varieties of LAV viruses and the like.

Figure 2:
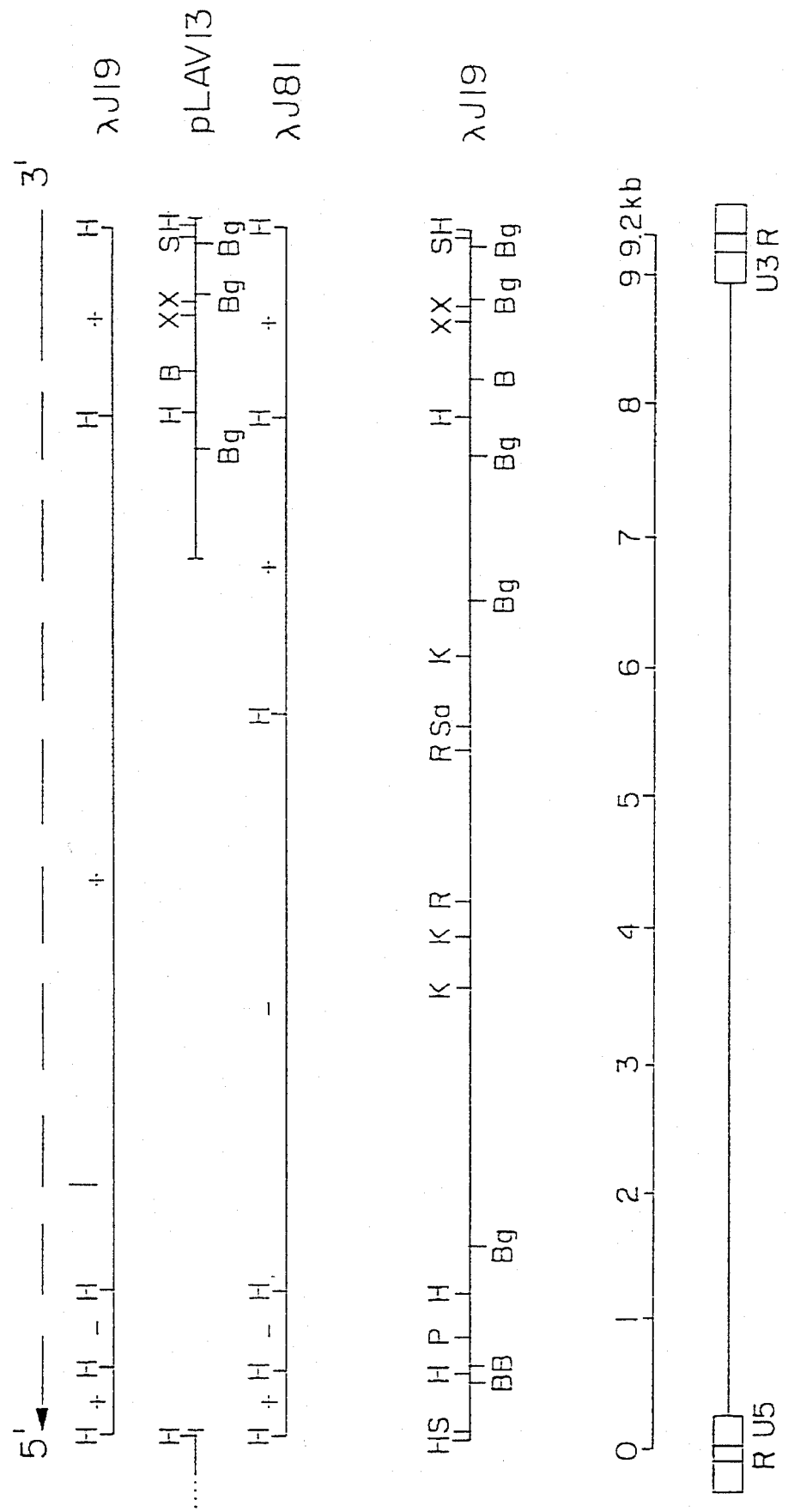
FIG. 2 shows the restriction charts of several cloned plasmids comprising the genome of LAV. The cDNAs comprise a total of 9.1 to 9.2 kb.

FIG. 2 is representative of restriction charts of several of these cDNAs comprising a total of 9.1 to 9.2 kb. More particularly, the polypeptides coded by cDNA fragments located in the region extending between the site KpnI (position 6100) with respect to restriction charts of FIG. 2 and site BglII (position 9150). The presence of a site characteristic of an antigen of the envelope of LAV or the like in the polypeptide which can be expressed (in a suitable host cell previously transformed by such a fragment or by a vector containing this fragment) can be detected by any suitable immunochemical means.

The antigens can also be used to separate antibodies having the above indicated characteristics from the polyclonal antibody mixture. In this case, the polypeptides can also be immobilized on an affinity chromatography support., for example, of the type indicated above. The process of separation will comprise contacting a solution containing the polyclonal antibodies with immobilized polypeptides, followed by recovering the antibodies retained by employing a solution or a buffer similar to that described above.

Finally, the invention relates to immunogenic composition characterized by the association of an antigen of the invention, and an immunogenic particle particularly in the proportion of 10 to 500, more particularly from 50 to 100 micrograms/kg, with a physiologically acceptable excipient permitting its administration to a living host, more particularly man, to confer on the host immunity with respect to said antigens, including the LAV viruses or entire analogs. These antigens comprise active principles whose immunogenicity can be employed any time that protection is sought in vivo against LAV viruses which are related to the immunogenic particles.

The invention also relates also to a process using the antigens of the invention for the detection of the presence of anti-LAV antibodies, particularly in blood specimens derived from man or from an animal, indicating the presence of AIDS or of LAS.

Finally, the invention relates to an in vitro process of diagnosis employing an envelope antigen of the invention for the detection of anti-LAV antibodies in the sera of patients afflicted with the disease or persons immunized against the virus. More particularly, the invention relates to a "kit" comprising this antigen.

The diagnostic method comprises:

depositing predetermined amounts of an antigen of the invention in the cup of a titration microplate:

adding increasing dilutions of the serum to be diagnosed into the cups;

incubating the microplate;

washing the microplate;

introducing into the cups of the microplate labeled antibodies of immunoglobulins of the blood, the label being an enzyme selected from enzymes capable of hydrolysing a substrate such that the substrate undergoes a modification of its absorption of radiations, at least within a predetermined band of wavelengths, and detecting, preferably comparatively with respect to a control, the amount of hydrolysis of the substrate as a measure of the potential risks or of the effective presence of the disease.

Of course, it is possible to carry out quantitative titrations of antibodies on the sera studied.

Preferred methods employ immuno-enzymatic or immunofluorescent titrations, in particular, employing the ELISA technique. Titrations may be determinations by immunofluorescence or direct or indirect immuno-enzymatic determinations.

We claim:

1. A method for the preparation of hybridomas which produce monoclonal antibodies specific for the human immunodeficiency virus type 1 (HIV-1) envelope glycoprotein, gp110, comprising the following steps:

(a) immunizing a mammal with HIV-1 gp110;

(b) isolating immunized splenocytes from said mammal;

(c) fusing the immunized splenocytes with a myeloma cell line to produce hybridomas;

(d) selecting for said hybridomas by culturing in selective media;

(e) clonally expanding said hybridomas in appropriate culture media; and, (f) identifying and characterizing those clones, or hybridomas, that produce monoclonal antibodies specific for HIV-1 gp110.

2. The method of claim 1 wherein the HIV-1 gp110-specific monoclonal antibodies produced by said hybridomas are isolated.

3. A method for the purification of the human immunodeficiency virus type 1 (HIV-1) envelope glycoprotein, gp110, employing monoclonal antibodies specific for HIV-1 gp110 comprising the following steps:

(a) immobilizing monoclonal antibodies specific for HIV-1 gp110 on a solid support;

(b) contacting a sample comprising HIV-1 gp110 with the immobilized monoclonal antibody of step (a), wherein said contact results in the formation of an antigen-antibody complex between said immobilized monoclonal antibody and said HIV-1 gp110;

(c) recovering and isolating said HIV-1 gp110 by dissociating the antigen-antibody complex of step (b) with a suitable buffer.

* * * * *

UNITED STATES PATENT AND TRADEMARK OFFICE
CERTIFICATE OF CORRECTION

PATENT NO. : 5,610,035
DATED : March 11, 1997
INVENTOR(S) : Luc MONTAGNIER, et al.

It is certified that error appears in the above-indentified patent and that said Letters Patent is hereby corrected as shown below:

ASSIGNEE, TITLE PAGE, line 1, after "Pasteur", insert --, and--.

ABSTRACT, TITLE PAGE, line 5, change "persistant" to --persistent--.

Claim 1, col. 8, line 34, before "steps", delete --the--.

Signed and Sealed this

Tenth Day of June, 1997

*Attest:*

BRUCE LEHMAN

*Attesting Officer*  Commissioner of Patents and Trademarks